(12) United States Patent
Hall et al.

(10) Patent No.: US 11,617,623 B2
(45) Date of Patent: Apr. 4, 2023

(54) VIRTUAL IMAGE WITH OPTICAL SHAPE SENSING DEVICE PERSPECTIVE

(71) Applicant: KONINKLIJKE PHILIPS N.V., Eindhoven (NL)

(72) Inventors: Christopher Stephen Hall, Kirkland, NY (US); Bharat Ramachandran, Morganville, NJ (US); Molly Lara Flexman, Melrose, MA (US); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1113 days.

(21) Appl. No.: 15/110,421

(22) PCT Filed: Jan. 4, 2015

(86) PCT No.: PCT/IB2015/050051
§ 371 (c)(1),
(2) Date: Jul. 8, 2016

(87) PCT Pub. No.: WO2015/110928
PCT Pub. Date: Jul. 30, 2015

(65) Prior Publication Data
US 2016/0331469 A1 Nov. 17, 2016

Related U.S. Application Data

(60) Provisional application No. 61/930,974, filed on Jan. 24, 2014.

(51) Int. Cl.
*A61B 8/12* (2006.01)
*A61B 34/20* (2016.01)
*A61B 8/08* (2006.01)
*A61B 8/00* (2006.01)
*A61B 5/06* (2006.01)
(Continued)

(52) U.S. Cl.
CPC .............. *A61B 34/20* (2016.02); *A61B 5/066* (2013.01); *A61B 8/0841* (2013.01);
(Continued)

(58) Field of Classification Search
None
See application file for complete search history.

(56) References Cited

U.S. PATENT DOCUMENTS 8,401,616 B2   3/2013   Verard et al.
9,861,271 B2   1/2018   Liu et al.
(Continued)

FOREIGN PATENT DOCUMENTS

JP   2001037756   2/2001
JP   2002119507 A  4/2002
(Continued)

*Primary Examiner* — Katherine L Fernandez
*Assistant Examiner* — Farouk A Bruce

(57) ABSTRACT

A system for providing a perspective for a virtual image includes an intraoperative imaging system (110) having a transducer (146) configured to generate an image data set for a region. A shape sensing enabled device (102) is configured to have at least a portion of the shape sensing enabled device positioned relative to the region. The shape sensing enabled device has a coordinate system registered with a coordinate system of the intraoperative imaging system. An image generation module (148) is configured to render a virtual image (152) of at least a portion of the region using the image data set wherein the virtual image includes a vantage point relative to a position on the shape sensing enabled device.

15 Claims, 5 Drawing Sheets

(51) Int. Cl.
  *A61B 8/14*    (2006.01)
  *G06T 19/00*   (2011.01)
  *G06T 7/30*    (2017.01)
  *G06T 7/70*    (2017.01)
  *A61B 34/30*   (2016.01)

(52) U.S. Cl.
  CPC .......... *A61B 8/0883* (2013.01); *A61B 8/0891* (2013.01); *A61B 8/12* (2013.01); *A61B 8/14* (2013.01); *A61B 8/4218* (2013.01); *A61B 8/4245* (2013.01); *A61B 8/4254* (2013.01); *A61B 8/523* (2013.01); *A61B 34/30* (2016.02); *G06T 7/30* (2017.01); *G06T 7/70* (2017.01); *G06T 19/00* (2013.01); *A61B 2034/2061* (2016.02)

(56) References Cited

U.S. PATENT DOCUMENTS

| | | |
|---|---|---|
| 2004/0015053 A1 | 1/2004 | Bieger et al. |
| 2004/0097805 A1 | 5/2004 | Verard |
| 2004/0106869 A1 | 6/2004 | Tepper |
| 2009/0314925 A1* | 12/2009 | Van Vorhis ............ A61B 34/20 250/203.2 |
| 2011/0015628 A1 | 1/2011 | Dalal |
| 2012/0289777 A1* | 11/2012 | Chopra .............. A61B 1/00009 600/109 |
| 2012/0289833 A1 | 11/2012 | Kashima |
| 2014/0142422 A1 | 5/2014 | Manzke et al. |
| 2014/0187919 A1 | 7/2014 | Parthasarathy et al. |
| 2014/0187949 A1* | 7/2014 | Zhao ....................... A61B 8/12 600/443 |
| 2014/0240713 A1* | 8/2014 | Kemp .................. A61B 8/0891 356/479 |
| 2016/0235496 A1 | 8/2016 | Hoffman et al. |
| 2017/0128144 A1 | 5/2017 | Hasser et al. |

FOREIGN PATENT DOCUMENTS

| | | |
|---|---|---|
| JP | 2011156286 | 8/2011 |
| JP | 2012055717 A | 3/2012 |

\* cited by examiner

VIRTUAL IMAGE WITH OPTICAL SHAPE SENSING DEVICE PERSPECTIVE

CROSS-REFERENCE TO PRIOR APPLICATIONS

This application is the U.S. National Phase application under 35 U.S.C. § 371 of International Application Serial No. PCT/IB2015/050051, filed on Jan. 4, 2015, which claims the benefit of U.S. Application Ser. No. 61/930,974, filed on Jan. 24, 2014. These applications are hereby incorporated by reference herein.

BACKGROUND

1. Technical Field

This disclosure relates to medical instruments and more particularly to the generation of virtual images within an image volume positioned from a vantage point of a shape sensing enabled instrument.

2. Description of the Related Art

A miniature ultrasound transducer at the tip of an intravascular medical device (such as a catheter) can provide useful clinical information. For example, intracardiac echocardiography (ICE) images can be used to understand anatomical information such as the structure of a heart. Intravascular ultrasound (IVUS) provides images of the blood column, endothelium, and plaque from within the blood vessel. There are disadvantages to the current implementation of IVUS and ICE. For example, IVUS imaging systems are very expensive (e.g., tens of thousands of dollars). There are also additional costs incurred due to the disposability of the IVUS catheter. The use of IVUS in a procedure can add time and risk to the procedure. There is also a desire to build IVUS technology into other devices (such as stent deployment devices or balloon catheters), but the size and complexity make this extremely challenging.

SUMMARY

In accordance with the present principles, a system for providing a perspective for a virtual image includes an intraoperative imaging system having a transducer configured to generate an image data set for a region. A shape sensing enabled device is configured to have at least a portion of the shape sensing enabled device positioned relative to the region. The shape sensing enabled device has a coordinate system registered with a coordinate system of the intraoperative imaging system. An image generation module is configured to render a virtual image of at least a portion of the region using the image data set wherein the virtual image includes a vantage point relative to a position on the shape sensing enabled device.

Another system for providing a perspective for a virtual image includes an intraoperative imaging system having a transducer configured to generate an image data set for a region. A shape sensing enabled device is configured to have at least a portion of the shape sensing enabled device positioned relative to the region, the shape sensing enabled device having a coordinate system registered with a coordinate system of the intraoperative imaging system. An image generation module is configured to render a virtual image of at least a portion of the region using the image data set wherein the virtual image includes a vantage point from a position on the shape sensing enabled device. A robot is configured to coordinate operation between the intraoperative imaging system and the shape sensing enabled device such that the robot maintains the shape sensing enabled device relative to the region during a procedure.

A method for virtual imaging includes imaging a region of a subject with an intraoperative imaging system to generate an image data set for the region; positioning at least a portion of a shape sensing enabled device relative to the region; registering a coordinate system of the shape sensing enabled device with a coordinate system of the intraoperative imaging system; and generating a virtual image of at least a portion of the region using the image data set wherein the virtual image includes a vantage point from a position on the shape sensing enabled device.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
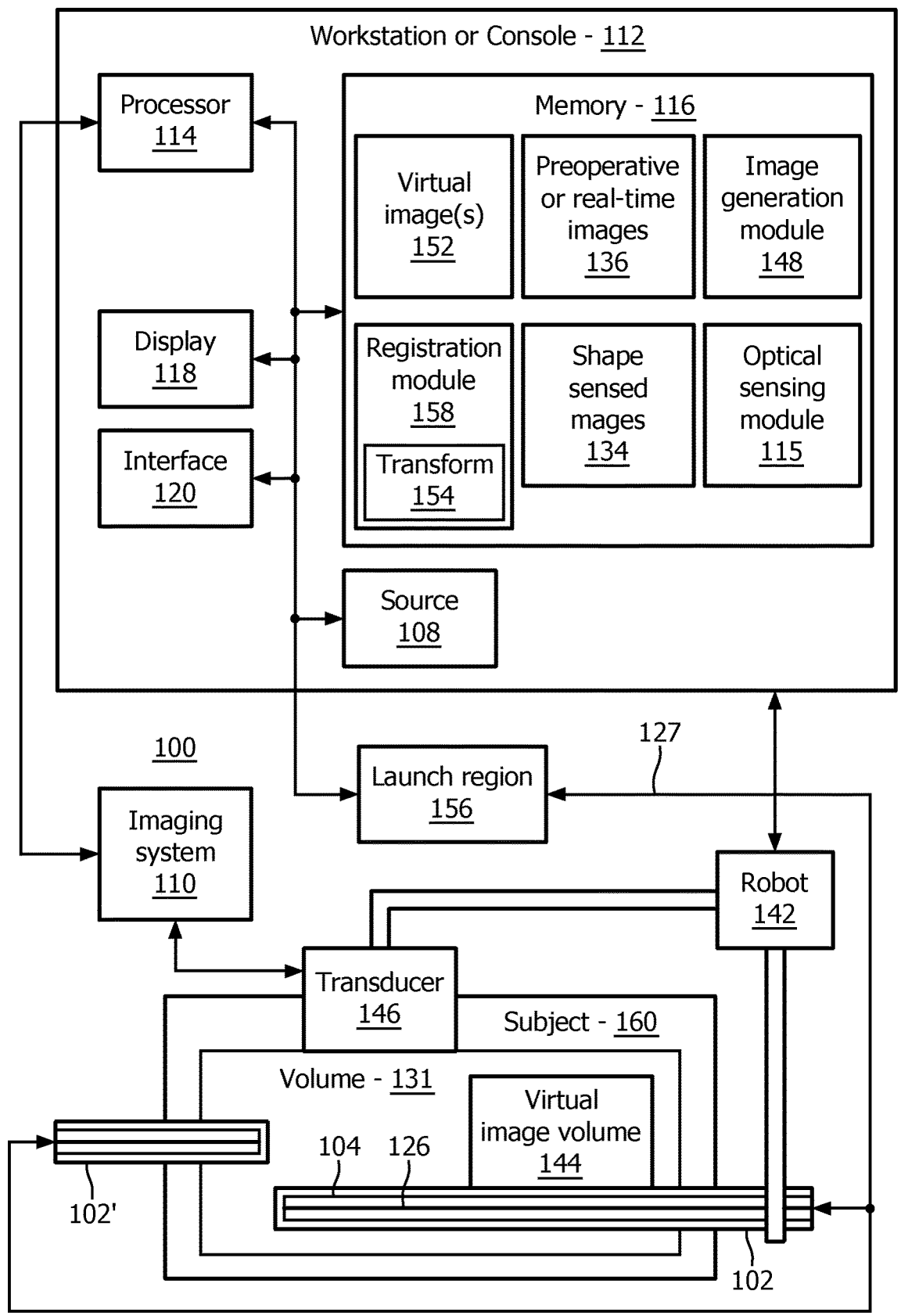
FIG. 1 is a block/flow diagram showing a shape sensing system providing a vantage point for a virtual image provided in an image volume in accordance with one embodiment.

In accordance with the present principles, systems, devices and methods are described which provide alternative approaches to placing a transducer (e.g., ultrasound) onto a tip of a probe, and instead employ an optical shape sensing catheter or other device together with a separate ultrasound imaging probe to recreate an image similar to that seen if the probe were to have ultrasound transducers on it. In this way, a virtual intracardiac echocardiography (ICE) image or virtual intravascular ultrasound (IVUS) image are provided such that optical shape sensing (OSS) catheters or other devices can be turned into ICE or IVUS catheters with the addition of an ultrasound imaging probe. These virtual images can expand usage in many different procedures, e.g., the use of virtual images generated by optical shape sensing or ultrasound can expand use cases for transesophageal echocardiography (TEE) probes into different areas of structural heart repair.

The present principles employ optical shape sensing to create a virtual ultrasound image. This may be done using a known transformation between an ultrasound probe and a catheter or shape sensing enabled device to reformat the ultrasound image so that the image appears as though a transducer aperture were on the catheter or device. The optical shape sensing catheter then can allow for the aperture to be translated and rotated about the catheter or relative to the catheter so long as the virtual aperture remains within the ultrasound dataset. Also, based on the position of the catheter in the ultrasound volume, the ultrasound transmit sequence can be adapted to optimize the virtual ultrasound image. To keep the catheter within the ultrasound imaging volume or at a position relative to the ultrasound imaging volume, the ultrasound imaging probe can be controlled manually by an operator, or robotically using a known position from the shape sensing catheter. The robotic control can improve generation of the virtual images by aligning the imaging volume to the device and allowing repositioning of the probe for the generation of a virtual volume.

Potential ultrasound image sources may include internal ultrasound probes, such as TEE, transrectal ultrasound (TRUS), etc.; single surface probes (e.g., linear, curved, sector, matrix); multiple surface probes (simultaneously or in sequence or both); etc. Potential registration between the ultrasound probe (e.g., head position) and the shape-sensing enabled device (e.g., catheter) may include shape-based sensing of the ultrasound probe (shape-to-shape registration prior to deployment); image-based registration of the ultrasonic probe (e.g., TEE probe head) using, e.g., EchoNav™, a model-based approach, x-ray based registration of the shape-sensed device, etc.; alternative tracking of the probe using technologies, such as, e.g., electromagnetic tracking of the TEE probe head (EM-to-shape registration prior to deployment), optical tracking of the hand-held probe, ultrasound-image based identification, etc.

The known position and plane of the device can be used to change the ultrasound transmit profile (through manual or robotic mechanical positioning or beam steering). Alternately, the ultrasound image could be used as input to drive the device towards the direction that is being visualized/targeted (for example, for IVUS pullback). The present principles permit any shape sensing enabled device to be transformed into an ICE or IVUS device with the addition of an external ultrasound probe. Any device already enabled for optical shape sensing for navigational purposes can be repurposed to perform virtual IVUS with the addition of a standard ultrasound imaging probe.

The present principles apply to any reformatting of an ultrasound volume or slice to create a virtual image with the transducer aperture position defined using optical shape sensing. This primarily applies to guide wires and catheters (manual and robotic), but could be extended to endoscopes, bronchoscopes, and other such devices or applications.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, heart, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for virtual image generation using shape sensing enabled devices is illustratively shown in accordance with an illustrative embodiment. System 100 may include a workstation or console 112 from which a procedure is supervised and/or managed. Workstation 112 preferably includes one or more processors 114 and memory 116 for storing programs and applications. Memory 116 may store an optical sensing module 115 configured to interpret optical feedback signals from a shape sensing device or system 104. Optical sensing module 115 is configured to use the optical signal feedback (and any other feedback, e.g., electromagnetic (EM) tracking, ultrasound, etc.) to reconstruct deformations, deflections and other changes associated with a medical device or instrument (shape-sensing enabled device or instrument) 102 and/or its surrounding region. The medical device 102 (and/or 102') may include a catheter, a guidewire, a probe, an endoscope, a robot, an electrode, a filter device, a balloon device, or other medical component, etc.

The shape sensing system 104 on device 102 (and/or 102') includes one or more optical fibers 126 which are coupled to the device 102 in a set pattern or patterns. The optical fibers 126 connect to the workstation 112 through cabling 127. The cabling 127 may include fiber optics, electrical connections, other instrumentation, etc., as needed.

Shape sensing system 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

Optical shape sensing (OSS) uses light along a multicore optical fiber for device localization and navigation during surgical intervention. The principle involved makes use of distributed strain measurement in the optical fiber using characteristic Rayleigh backscatter or controlled grating patterns. The shape along the optical fiber begins at a specific point along the sensor, known as a launch region 156 or z=0, and the subsequent shape position and orientation are relative to that point. Optical shape sensing fibers integrated into medical devices, such as catheters and guidewires, provide live guidance of the devices during minimally invasive procedures and can provide the position and orientation of the entire device 102.

In one embodiment, workstation 112 includes an image generation module 148 configured to receive feedback from the shape sensing device 104 (position data) as to where the sensing device 104 is or has been in a subject 160. An image volume (or data set) 131 is imaged within the subject 160 using an imaging system 110, such as an ultrasound imaging system, although other intraoperative imaging systems may be employed. An image or images 134 of a data set is/are collected from the imaging system 110 using one or more internal or external probes or transducers 146 to map out the image volume 131. The images 134 can be displayed on a display device 118. The images 134 may be overlaid on, fused with or otherwise depicted along with other preoperative or intra-operative images.

Workstation 112 includes the display 118 for viewing internal images of a subject (patient or other object) 160 or volume 131. Display 118 may also permit a user to interact with the workstation 112 and its components and functions or any other element within the system 100. This is further facilitated by an interface 120 which may include a keyboard, mouse, a joystick, a haptic device, or any other peripheral or control to permit user feedback from and interaction with the workstation 112.

Conventional intravascular ultrasound (IVUS) uses a miniaturized ultrasound transducer at a distal tip of a catheter to perform ultrasound imaging of the vasculature. IVUS imaging can be integrated into the catheter in different ways to perform either side-facing (or concentric) imaging or forward-facing imaging of the vessel. IVUS is most commonly used to visualize the endothelium of the blood vessels. This is typically used to determine the amount of plaque in a given vessel or the degree of stenosis. The most common use of IVUS is in cardiac applications, for example, imaging of the coronary arteries. A conventional intracardiac echocardiography (ICE) catheter may be introduced into the heart for real-time anatomical imaging. ICE is commonly used in electrophysiology procedures to localize anatomical structures, devices, and monitor radiofrequency energy delivery during ablation.

In accordance with the present principles, virtual IVUS and/or ICE (and other operations) can be performed using the shape sensing enabled device 102 (and/or 102') and an ultrasound probe or transducer 146. The ultrasound probe 146 may be coupled to an ultrasound imaging system 110, which may be part of the console 112 or may be a separate unit. The optical shape sensing of device 102 is employed to resample an ultrasound dataset to create a virtual ultrasound image 152 from a virtual ultrasound volume 144. This is done using a known transformation (transform 154, stored in a registration module 158 or stored elsewhere in memory 116) between the ultrasound probe 146 and the optical shape sensing fiber 126 (coupled to or in the device 102, such as a catheter) to reformat the ultrasound image to form the virtual image 152 so that it appears as though the transducer aperture is on or has a known transformation to the device 102 or catheter. The virtual image 152 is generated from a vantage point of a known position of the shape sensing enabled device 102. The shape sensing enabled device 102 may be inside or outside of an image volume 144 employed to generate the virtual image 152. The shape sensing enabled device 102 need not be present within a virtual image volume (slice or plane) 144 but can be positioned relative to the image volume 144 and may be outside the image volume 144.

The virtual image volume 144 is generated within the ultrasound dataset volume 131. The virtual image volume 144 may be selected or generated in a plurality of ways. These may include one or more of the following. The virtual image volume 144 can include a pre-set configuration (e.g., shape and size). The shape and size may be selected in accordance with the requirements for IVUS, ICE or other procedure or application. The properties of the image 152 may be user-configurable including depth, field of view (FOV), two-dimensional (2D), 3D, circumferential, distance along a catheter, etc., and the image volume 144 is configured accordingly. The virtual image volume 144 may include an automated slice selection based on a shape of the shape-sensed device 102.

The virtual image volume 144 may have an automated volume selection based on features detected in an image (for cardiac applications, e.g., a heart chamber, etc.). In one embodiment, an interactive volume may be displayed on the display 118 that the user can drag to various locations along the device 102, rotate around the device, scale (for example by scrolling the mouse), etc. The virtual image volume 144 may be sized or optimized to capture two (or more) devices (102, 102') within the volume or slice or optimized so that, with two devices, one device 102' becomes a vantage point, and the other device is visualized within the virtual image volume 144. Devices 102 and/or 102' may be inside or outside of the image volume 144.

In one embodiment, multiple OSS devices 102, 102', etc. may be employed. The devices 102, 102' may be employed to create a composite virtual image volume 144 where each device contributes a portion of the virtual image volume 144. One device 102' may be employed as a vantage point for the other device which may be visualized within the virtual image volume 144. In another embodiment, imaging for valve or stent placement may be provided, where the shape sensing enabled device 102 acts as a stiff wire, and the valve or stent is brought over the stiff wire. The virtual image volume 144 may be selected at a known offset from the OSS wire 102, which has the valve. In this case, no portion of the OSS device 102 will be within the image volume 144, but a known transformation to a virtual slice, plane or volume within the virtual image volume 144 is known.

A registration module 158 is configured to register the coordinate system of the imaging device 110 and/or the imaging transducer or probe 146 and a coordinate system of the shape sensing enabled device 102 or the shape sensing fiber(s) 126. The transform 154 provides coordinate translation between these coordinates systems. The transform 154 may be employed by the image generation module 148 to generate the virtual image 152 as will be described in greater detail herein. A robot 142 may be employed to coordinate operations and registration between the probe(s) or transducer(s) 146 and the shape sensing enabled device 102.

Figure 2A:
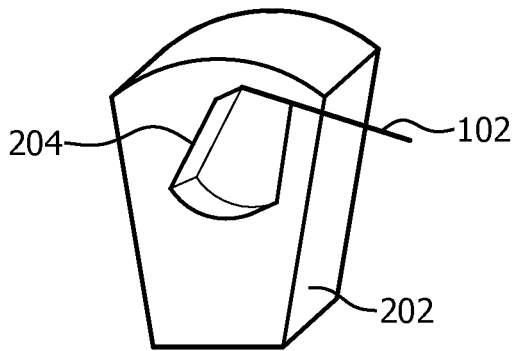
FIG. 2A is a perspective view of an image volume having a shape sensing enabled device providing a vantage point for imaging a side-facing volume in accordance with one embodiment.
Figure 2B:
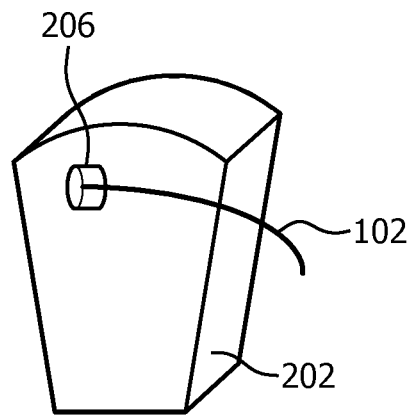
FIG. 2B is a perspective view of an image volume having a shape sensing enabled device providing a vantage point for imaging a circumferential volume in accordance with one embodiment.
Figure 2C:
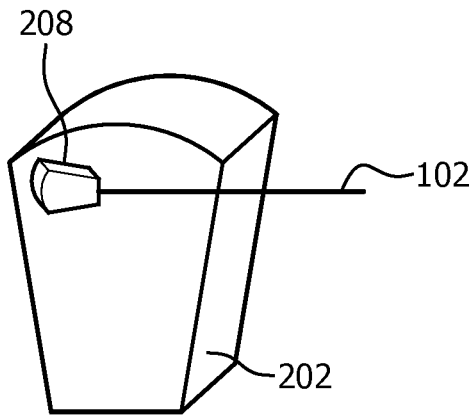
FIG. 2C is a perspective view of an image volume having a shape sensing enabled device providing a vantage point for imaging a front-facing volume in accordance with one embodiment.

Referring to FIGS. 2A-2C, possible virtual imaging volumes 204, 206 and 208 are shown resampled from an original ultrasound image volume 202 as examples of ultrasound image resampling to convert an image from a TEE or external probe into a virtual ICE or IVUS image. The imaging volumes 204, 206 and 208 can include a side-looking image volume as in ICE (FIG. 2A), a circumferential image as in IVUS (FIG. 2B), or a forward-looking image volume (FIG. 2C). The forward-looking image (FIG. 2C) may be used to give endoluminal views, and may also be pulled back from the very tip of the device 102 to give a 'first-person' perspective of both the instrument 102 and the ultrasound image of the anatomy being imaged. It should be understood that image planes or slices (two-dimensional) images may also be employed instead of or in addition to the image volumes described above.

In one embodiment, the optical shape sensing catheter 102 permits a virtual ultrasound aperture to be translated along and rotated about the catheter 102 so long as the virtual aperture and image field of view remains within the ultrasound dataset (e.g., volume 202).

Figure 3:
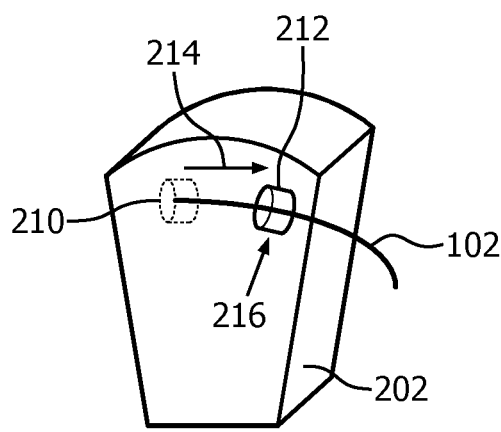
FIG. 3 is a perspective view of an image volume having a shape sensing enabled device providing a vantage point for pull-back imaging in accordance with one embodiment.

Referring to FIG. 3, another US volume 202 includes a shape sensing enabled catheter 102 which is moved from a first position 210 of a virtual image volume 216 to a second position 212 of the image volume 216 in a direction of arrow 214. FIG. 3 shows a virtual IVUS pullback where the operator can slide the virtual aperture along the catheter 102 or other device.

The ultrasound image can be generated from a single transducer, e.g., a transesophageal echocardiogram (TEE) transducer, nasal TEE probe, or an external surface probe (such as, a C5-2 probe, etc.). Further, multiple transducers can also be employed to track the catheter 102 over a larger region. These embodiments are shown with reference to FIGS. 4-6. Multiple transducers/sources may be employed using a position of the OSS fiber to select which probe to use as the imaging source. Further, multiple sources can be employed to stitch the image between the field of view of each transducer. The position of the OSS fiber can also be used to steer a beam of the ultrasound probes to enhance image compounding in the region of interest (the location of the device).

Figure 4:
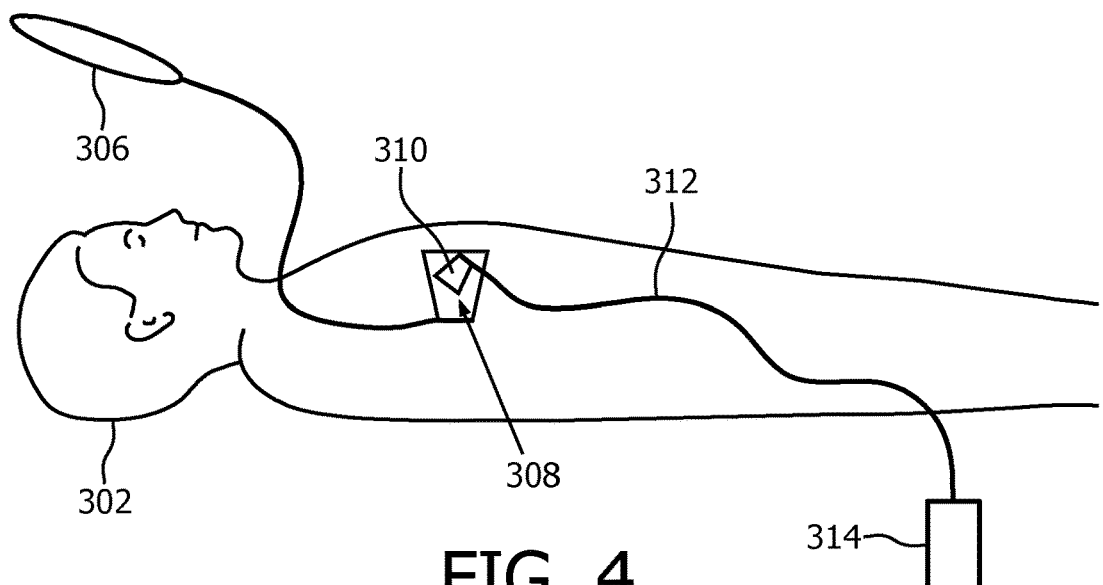
FIG. 4 is a cross-sectional view of a subject showing an internally disposed transducer having a shape sensing enabled device providing a vantage point for imaging a volume in accordance with one embodiment.

Referring to FIG. 4, a cross-sectional diagram shows a patient 302 having a TEE transducer 304 on a TEE probe 306. The transducer 304 is passed through the esophagus of the patient 302 and creates an ultrasonic imaging volume 308 within the patient 302. The imaging volume 308 overlaps a region or regions in which a shape sensing enabled device 314 (e.g., a catheter) has an optical shape sensing fiber 312 therein. The device 314 may be provided through a port or through a natural orifice in the patient. A virtual image volume 310 (e.g., virtual ICE or virtual IVUS device) is obtained using at least a portion of the data set of the imaging volume 308. The virtual image volume 310 is anchored at a selected location and orientation along the device 314 and within the imaging volume 308. A virtual image of the virtual image volume 310 can be provided from a vantage point on the shape sensing enabled device 314.

Figure 5:
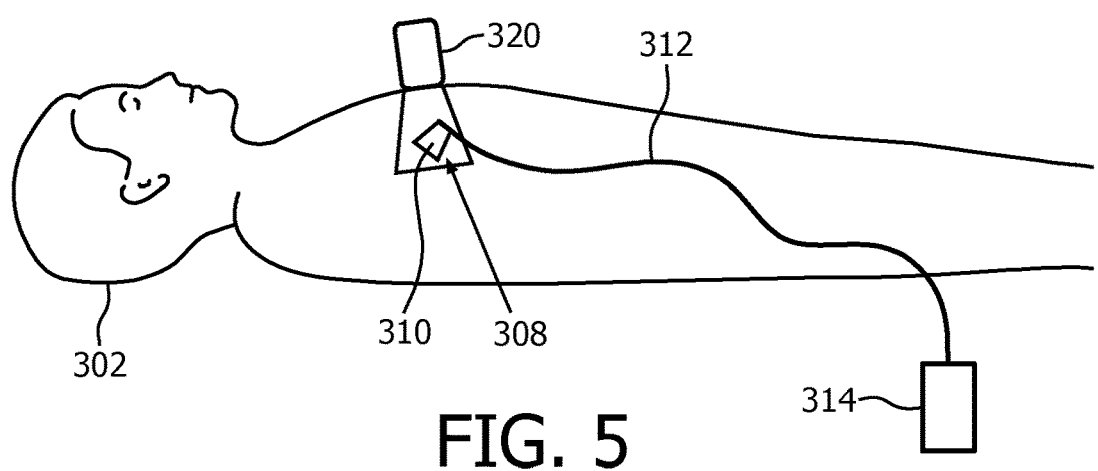
FIG. 5 is a cross-sectional view of a subject showing an externally disposed transducer having a shape sensing enabled device providing a vantage point for imaging a volume in accordance with one embodiment.

Referring to FIG. 5, a cross-sectional diagram shows the patient 302 with a single external transducer 320 (probe) for generating the ultrasonic imaging volume 308 within the patient 306. The imaging volume 308 overlaps a region or regions in which the shape sensing enabled device 314 (e.g., a catheter) has the optical shape sensing fiber 312 therein. The virtual image volume 310 (e.g., virtual ICE or virtual IVUS device) is obtained using at least a portion of the data set of the imaging volume 308. The virtual image volume 310 is anchored at a selected location and orientation along the device 314 and within the imaging volume 308.

Figure 6:
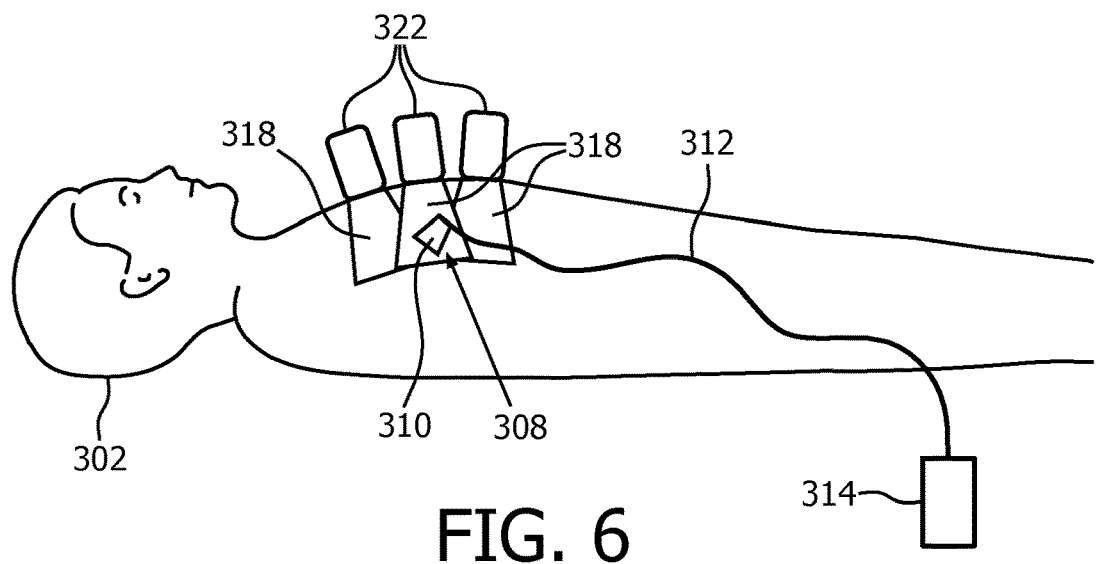
FIG. 6 is a cross-sectional view of a subject showing a plurality of externally disposed transducers having a shape sensing enabled device providing a vantage point for imaging a volume in accordance with one embodiment.

Referring to FIG. 6, a cross-sectional diagram shows the patient 302 with a plurality of external transducers 322 for generating multiple ultrasound apertures (windows) 318 for the ultrasonic imaging volume 308 within the patient 306. The imaging volume 308 includes a region of combined windows 318 that overlaps a region or regions in which the shape sensing enabled device 314 (e.g., a catheter) has the optical shape sensing fiber 312 therein. The virtual image volume 310 (e.g., virtual ICE or virtual IVUS device) is obtained using at least a portion of the data set of the imaging volume 308. The virtual image volume 310 is anchored at a selected location and orientation along the device 314 and within the imaging volume 308.

To resample the ultrasound image to obtain the virtual image volume 310, it is necessary to know the transformation between an ultrasound transducer aperture for the image volume 308 and a virtual aperture for the virtual image volume 310. In particularly useful embodiments, the following methods may be employed for obtaining this transformation. In one embodiment, a shape sensed transducer (internal or external) and a shape sensed catheter may be provided. In this case, one way of registering the two shape sensing coordinate systems is, prior to a procedure, launch fixtures of the two shape sensed devices are registered together using a point based registration or a shape-based registration.

In another embodiment, a fluoroscopy-based registration may be performed. For example, a TEE probe head can be registered to an x-ray image (for example, as in EchoNav™) and the OSS catheter can be registered to the x-ray image as well, providing a transformation between the TEE probe head and the OSS device. The TEE probe head would need to be tracked dynamically via x-ray whereas the OSS device only needs to be registered to the x-ray image once. In yet another embodiment, an alternatively tracked transducer and a shape sensed catheter may be employed. A transducer head can be tracked using other tracking technologies (e.g., electromagnetic tracking or optical tracking for an external transducer) and a launch fixture of the optical shape sensing device can be registered to that alternate tracking solution. Other registration techniques and methods are also possible and are contemplated in accordance with the present principles.

The embodiments described above may include robotically controlled ultrasound tracking of a virtual ICE/IVUS catheter. The virtual ICE/IVUS catheter works when the virtual image lies within the ultrasound field of view. Therefore, an ultrasound operator needs to position the ultrasound probe so that the correct portion of the catheter is within the field of view. To reduce the impact on the clinical workflow, the ultrasound probe(s) (304, 320, 322) can be robotically controlled to maintain the catheter position within the ultrasound dataset. In the event that ultrasound quality degrades or is lost due to lack of coupling or pressure between the ultrasound transducer head and the surface (detected via image processing or manual observation), a robot can detect and compensate for this (by, e.g., increasing pressure or releasing gel to the surface) and then continuing to perform imaging. The robotic control can concurrently maintain the virtual imaging volume 310 within the ultrasound dataset 308, can optimize a physical position of the transducer 304, 320 or 322 for the virtual image resolution, and can work within the physical constraints of the clinical application to maintain suitable contact with the tissue for imaging, while minimizing the forces on the patient 302. In the case of robotically controlled TEE probe 306, the control of the robot may include control of two dials changing position of the curved probe tip.

Figure 7A:
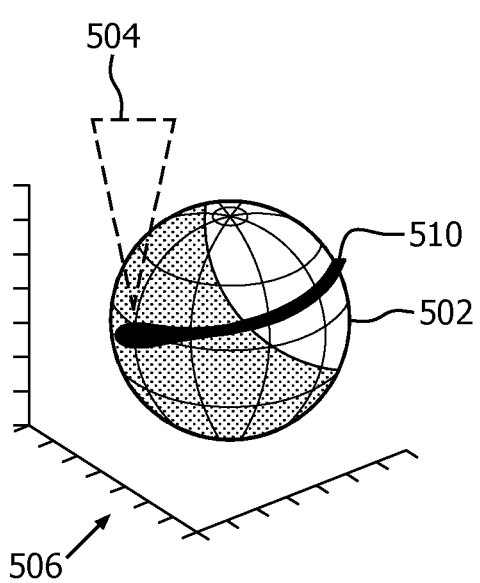
FIG. 7A is a diagram showing a starting image for showing a range of motion possible by a probe in accordance with the present principles.
Figure 7B:
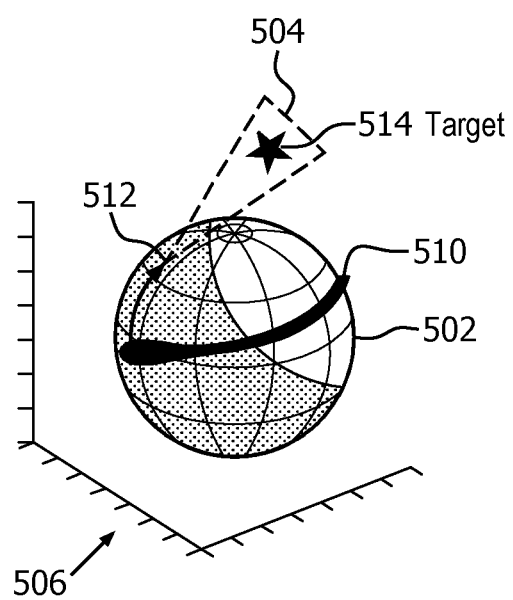
FIG. 7B is a diagram showing a target image for showing the range of motion possible by a probe in accordance with the present principles.

Referring to FIGS. 7A and 7B, an experimental result is shown demonstrating range of motion of a TEE probe tip when controlled with dials (not shown). A system to control the dials on the handle of TEE probe robotically controls the position of a steerable probe tip. In the case of a robotically controlled TEE probe, the control of the robot (142, FIG. 1) may include control of the two dials for changing position of a curved probe tip 510.

The illustrations of the range of motion possible by a TEE probe, and the motion needed to move from a starting image (FIG. 7A) to a target image (FIG. 7B) are shown. Every point on a sphere 502 will have an inherent orientation of a probe head 510 with a corresponding image volume 504. The points of the sphere 502 and volume orientations associated with those points are a characteristic of the probe 510 and can be stored in a robot control system in a lookup table or transform. Once a target 514 is selected in a coordinate frame 506 of the robot, an ideal orientation 512 of the ultrasound (US) volume is computed so that the target 514 is in the middle of the volume 504. This orientation 512 is matched to the closest orientation in the lookup table, which is matched to the position of the probe 510. The robot attempts to reach that position by controlling control dials while limiting force to tissue. If no excessive force is applied in the motion, the robot will reach the most optimal position to view the target 504. If the force limit is reached, the viewpoint of the imaging device will be suboptimal but optimized given the constraints.

Robotic control of imaging devices may have a multitude of implementations for control of ultrasound probes. For example, a system to control the dials on the handle of TEE probes and robotically control the position of the steerable probe tip may be employed, as well as other robot systems and methods.

Figure 8:
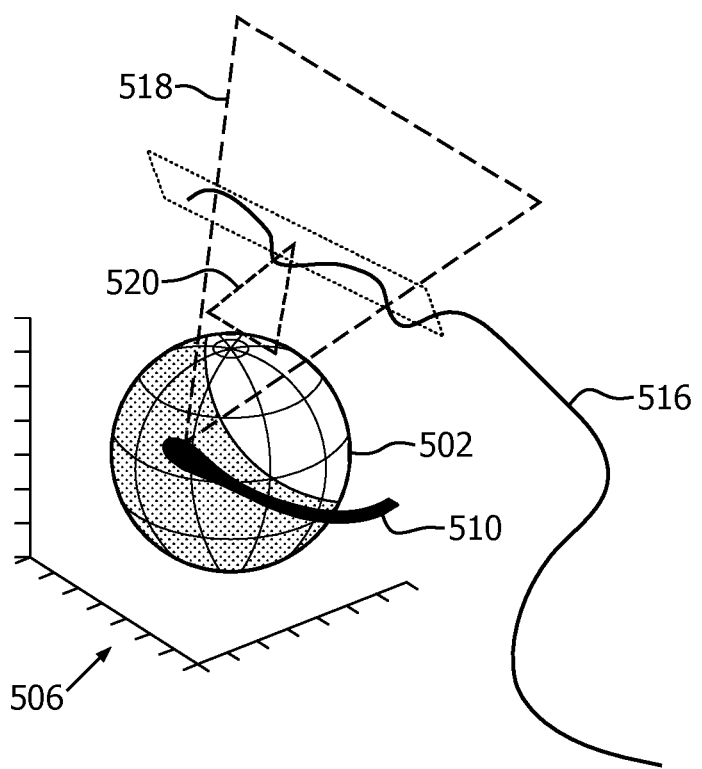
FIG. 8 is a diagram showing generation of a virtual view in a correct plane of a catheter in accordance with the present principles.

Referring to FIG. 8, to allow an appropriate generation of a virtual view in a correct plane of the catheter, the control scheme can be modified so that the US probe 510 is guided from a shape of the proximal end of a catheter 516. In this embodiment, the shape of the catheter 516 is fit to a plane 518. The orientation of the plane 518 to the points in the probe workspace is optimized so that an angle between a virtual image plane 520 and a physical image plane 518 is minimized and so that the size of the virtual image volume 520 is maximized.

In a further embodiment, the robot can move to an optimal position to generate a virtual ultrasound volume and then go back to the original position to visualize some other features (e.g. another device or a valve). The optimal plane may be determined through the distal portion of the device 516 to determine the optimal position of the probe head 510. Since this motion will be known from robot encoders and robot workspace, the relationship between the physical (518) and virtual (520) volumes can also be known and visualized in the same reference frame. Those parts of the virtual volume that are visible in the new probe position can be updated from the physical volume and shown in context of the "off-line" volume visualization. The robot can be moved between two different positions to update the entire volume.

The virtual ICE/IVUS image will likely not be aligned in a same orientation as the original ultrasound image. As a result, the resolution of the resampled image may be suboptimal. Optimization of the ultrasound acquisition could be addressed by one or more of the following items. The position of the ultrasound transducer can be physically adjusted so that a highest resolution sampling is in-plane and in-direction with the virtual image. This could be done by giving visual feedback to the operator, or by making use of robotic control as described above. Another method includes adapting the transducer transmit profile so that the highest resolution directions are in-plane with the virtual ICE or virtual IVUS images or using beam forming schemes or compounding schemes. Better resolution can also be achieved by decreasing of the field of view to only the necessary 3D ultrasound volume so that the frame rate can be increased or multiple beam angles can be used. Combinations of the above methods may also be employed to optimize resolution.

Figure 9:
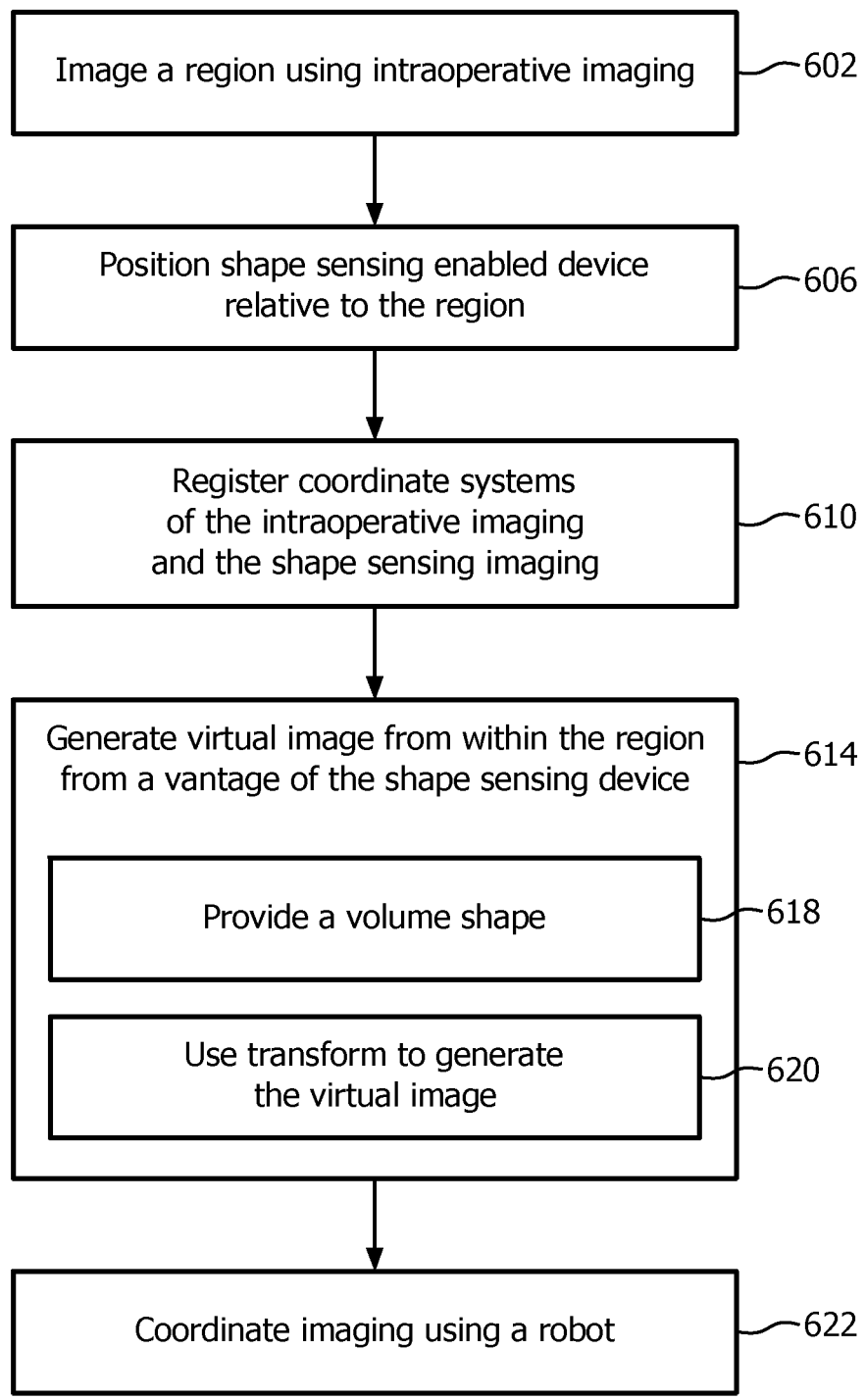
FIG. 9 is a flow diagram showing a method for virtual imaging in accordance with an illustrative embodiment.

Referring to FIG. 9, a method for virtual imaging is illustratively depicted in accordance with the present principles. In block 602, a region of a subject is imaged with an intraoperative imaging system to generate an image data set for the region. In block 606, at least a portion of a shape sensing enabled device is positioned as a vantage point within the region or outside of the region. The shape sensing enabled device or devices may include optical fiber(s), and the intraoperative imaging system may include an ultrasonic imaging system. The ultrasonic imaging system may include one or more ultrasonic transducers internally or externally disposed within a subject to be imaged.

In block 610, a coordinate system of the shape sensing enabled device is registered with a coordinate system of the intraoperative imaging system. The registering may include at least one of: shape-based (e.g., shape-to-shape) registration, image-based registration and tracking technology registration. Other registration techniques may also be employed.

In block 614, a virtual image of at least a portion of the region is generated using the image data set wherein the virtual image includes a vantage point from a position of the shape sensing enabled device. In block 618, the virtual image may include a virtual image volume, plane or slice(s) having a shape that includes at least one of: a side-looking image, a circumferential image and a forward-looking image. Other geometries may also be provided for the virtual image volume. These may be user-configured, pre-set, slices, etc.

In block 620, the virtual image may be generated by employing a transform or transforms configured to transform the image data set (or the region) to the virtual image. In block 622, operations between the intraoperative imaging system and the shape sensing enabled device may be coordinated using a robot. For example, a robot may move the US transducer relative to a catheter or other device to ensure coordination between the systems. The robot positions the imaging transducer so that it follows the OSS device and maintains the necessary or desired virtual image.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for virtual image with optical shape sensing device perspective (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for providing a perspective for a virtual image, comprising:
   an intraoperative imaging system having a transducer configured to generate an image data set for a region;
   a shape sensing enabled device, which includes at least one optical shape sensing fiber and is configured to have at least a portion of the shape sensing enabled device positioned relative to the region, the shape sensing enabled device having a coordinate system registered with a coordinate system of the intraoperative imaging system; and
   a workstation comprising a processor and a memory that stores instructions, which when executed by the processor, cause the processor to: determine a vantage point corresponding to an aperture of the transducer as being on or having a known transformation to the shape sensing enabled device, wherein the vantage point is determined relative to the shape sensing enabled device based on shape sensing information obtained from the at least one optical fiber; and
   render, from the vantage point determined by shape sensing information obtained from the at least one optical fiber, the virtual image of at least a portion of the region using the image data set.

2. The system as recited in claim 1, wherein the virtual image includes at least one of: a side-looking image, a circumferential image and a forward-looking image.

3. The system as recited in claim 1, wherein the virtual image includes one or more two-dimensional image slices.

4. The system as recited in claim 1, wherein the intraoperative imaging system includes an ultrasonic imaging system and the transducer includes one or more ultrasonic transducers internally disposed within or externally mounted on a subject to be imaged.

5. The system as recited in claim 1, further comprising a registration module for registering the coordinate system of the shape sensing enabled device with the coordinate system of the intraoperative imaging system, and including a transform configured to transform the image data set to the virtual image.

6. The system as recited in claim 1, further comprising a robot configured to coordinate operation between the intraoperative imaging system and the shape sensing enabled device to maintain an image relative to the shape sensing enabled device during a procedure.

7. The system as recited in claim 1, wherein registration between the intraoperative imaging system and the shape sensing enabled device includes at least one of:
shape-based registration, image-based registration and tracking technology registration.

8. The system as recited in claim 1, wherein, when rendering the virtual image, an angle between a virtual image plane for the virtual image and a physical image plane for a physical image is minimized, so that a size of a virtual image volume is maximized.

9. A method for virtual imaging, comprising:
imaging a region of a subject with an intraoperative imaging system having a transducer to generate an image data set for the region;
positioning at least a portion of a shape sensing enabled device which includes at least one optical shape sensing fiber relative to the region;
registering a coordinate system of the shape sensing enabled device with a coordinate system of the intraoperative imaging system;
determining a vantage point corresponding to an aperture of the transducer as being on or having a known transformation to the shape sensing enable device, wherein the vantage point is determined relative to the shape sensing enabled device based on shape sensing information obtained from the at least one optical fiber; and
generating, from the vantage point determined by shape sensing information obtained from the at least one optical fiber, a virtual image of at least a portion of the region using the image data set.

10. The method as recited in claim 9, wherein generating a virtual image includes generating the virtual image including at least one of: a side-looking image, a circumferential image and a forward-looking image.

11. The method as recited in claim 9, wherein the virtual image includes at least one of: a side-looking image, a circumferential image and a forward-looking image.

12. The method as recited in claim 9, wherein the virtual image includes one or more two-dimensional image slices.

13. The method as recited in claim 9, further comprising registering the coordinate system of the shape sensing enabled device with the coordinate system of the intraoperative imaging system, and including a transform configured to transform the image data set to the virtual image.

14. The method as recited in claim 9, wherein registering between the intraoperative imaging system and the shape sensing enabled device includes at least one of: shape-based registration, image-based registration and tracking technology registration.

15. The method as recited in claim 9, further comprising: minimizing an angle between a virtual image plane for the virtual image and a physical image plane for a physical image when generating the virtual image, so that a size of a virtual image volume is maximized.

* * * * *